United States Patent [19]

Connor et al.

[11] Patent Number: 5,338,491
[45] Date of Patent: Aug. 16, 1994

[54] CLEANING COMPOSITIONS WITH GLYCEROL AMIDES

[75] Inventors: Daniel S. Connor; Jeffrey J. Scheibel, both of Cincinnati; Yi-Chang Fu, Wyoming; Bruce P. Murch, Cincinnati; Randall A. Watson, Cincinnati; Kirsten L. McKillop, Cincinnati, all of Ohio

[73] Assignee: The Proctor & Gamble Co., Cincinnati, Ohio

[21] Appl. No.: 20,513

[22] Filed: Feb. 22, 1993

Related U.S. Application Data

[62] Division of Ser. No. 857,887, Mar. 26, 1992, Pat. No. 5,223,179.

[51] Int. Cl.$^5$ ............................ C11D 3/32; C11D 1/66
[52] U.S. Cl. ............................ 252/548; 252/DIG. 13; 252/DIG. 14; 252/550
[58] Field of Search ....... 252/548, DIG. 13, DIG. 14; 260/404

[56] References Cited

U.S. PATENT DOCUMENTS

| | | | |
|---|---|---|---|
| 2,703,798 | 3/1955 | Schwartz | 252/548 |
| 3,439,007 | 4/1969 | Milks | 260/404 |
| 4,183,815 | 1/1980 | Wixon et al. | 252/8.8 |
| 4,321,157 | 3/1982 | Harris et al. | 252/174.25 |
| 5,223,179 | 6/1993 | Connor et al. | 252/548 |

*Primary Examiner*—Paul Lieberman
*Assistant Examiner*—E. M. Higgins
*Attorney, Agent, or Firm*—Jerry J. Yetter; George W. Allen

[57] ABSTRACT

Detergent compositions containing N-(1,2 propanediol) fatty acid amide surfactants of the general type $RC(O)NR^1CH_2CHOHCH_2OH$, especially where $R^1$ is methyl or hydroxyethyl, are useful surfactants in laundry detergents, dishwashing liquids, shampoos, bar soaps, and hard surface cleaners. The amide surfactants provide good cleaning even in the absence of LAS surfactants.

13 Claims, No Drawings

CLEANING COMPOSITIONS WITH GLYCEROL AMIDES

This is a division of application Ser. No. 07/857,887, filed on Mar. 26, 1992 now U.S. Pat. No. 5,223,179.

TECHNICAL FIELD

The present invention relates to processes and compositions for cleaning fabrics, hard surfaces and the like using glycerol amides, a.k.a. N-(1,2-propanediol) fatty acid amides, as detersive surfactants.

BACKGROUND OF THE INVENTION

A wide variety of detersive surfactants are known in the literature and in commercial practice. Such surfactants range from common soap to sophisticated betaine and sulfobetaine synthetic surfactants. In general, the continuing search for new detersive surfactants has been the result of the desires of the formulator to meet a growing list of cleaning needs under a wide variety of conditions. Thus, the formulator of laundry detergents must provide products which remove from fabrics a wide variety of soils and stains, ranging from petroleum oils and fatty oils to proteins, carbohydrates, clay and other particulate soils, and mixtures of such soils and stains. Moreover, users of laundry detergents often employ widely disparate laundering conditions, ranging from cold water washing to hot water washing. Since usage habits are becoming less and less uniform, formulators are also required to provide the consumer with products which function well with a wide variety of soils and under a wide variety of usage conditions.

In addition to the above-noted considerations, the formulators of laundry detergents in many areas of the world now find themselves prevented by various regulations from using phosphate detergency builders. Since phosphate builders were a mainstay for many heavy duty laundry detergents, their removal from consumer products has required very substantial reformulation efforts, especially for heavy duty laundry detergents.

Moreover, there is increasingly a perceived need to provide stable, effective detergent compositions which are formulated from renewable resources which do not rely on petrochemicals. In addition, there is a need to provide detergent formulations containing ingredients which perform well in combination with alkyl benzene sulfonate ("LAS") surfactants. Alternatively, the present invention provides high cleaning compositions which do not require the presence of LAS. This is particularly advantageous to formulators who wish to include detersive enzymes in their products, especially heavy duty liquid fabric laundering products, since LAS can degrade and deactivate such enzymes.

The present invention employs the fatty acid amides of glycerol amines to address the aforementioned issues. Such amides provide substantial cleaning advantages, especially when used in conjunction with other detersive surfactants. Furthermore, such amides mainly comprise fatty acid units and glycerol units which, themselves, are available from renewable resources such as plant and animal fats and oils. The amides herein also exhibit sudsing benefits which exceed those of comparable ethanolamides, and demonstrate distinct advantages in solubility and formulatability in "light-duty" liquid detergent compositions, such as hand dishwashing liquids.

BACKGROUND ART

The following references are instructive with regard to the present invention: British Patent 1,341,937, to Jefferson Chemical Co., published Dec. 12, 1973; 3,424,680, issued Jan. 28, 1969, to van Loo, et al; U.S. Pat. No. 3,439,007, issued Apr. 15, 1969, to John Edward Milks; U.S. Pat. No. 3,644,204, issued Feb. 22, 1972, to Heins, et al; EPO Application 282816, Sep. 21, 1988, Yano, Shinji et al; Japanese 87-158684, Jun. 25, 1987, Kao Corp.; Japanese 5 212 6500, Oct. 24, 1977; Japanese 0 100 9908, Jan. 13, 1989, Kao Corp.; Oette and Ischung German Patent DE 282 0892, Nov. 22, 1979; Weiss, et al.; German 2 106 383; and German 2 343 786; Siegrist, et al; Rahman, M. D., et al, *J. Med. Chem.* 31(8), 1656–9; Imokawa, G., et al, *J. Soc. Cosmet, Chem.*, 40(5), 273–85 (1989); Dijkman, R., et al, *Biochim. Biophys. Acta*, 1043(1), 67–74; Coleman, R. A., *Biochim. Biophys. Acta*, 963(2), 367–74; Parinandi, N. L., et al, *FEBS Lett.*, 237(1-2), 49–52; and Marx, M. H., et al *J. Med. Chem.* 31(4), 858–63.

Various compositions containing fatty acid amides of polyhydroxyamines having three or more hydroxyl substituents attached to a carbon chain affixed to said amine are known. The amides used herein have the advantage over such amides tri- and higher polyhydroxy that they do not tend to gel as much, nor do they tend to cyclize and form less biodegradable by-products during manufacture and processing. By contrast with unsubstituted glycerol amides whose Krafft temperatures are excessively high, the amides used herein which contain $R^1$ groups other than hydrogen are soluble and easy to formulate into finished cleaning compositions.

SUMMARY OF THE INVENTION

The present invention relates to cleaning compositions comprising:
(a) from about 1% to about 30% by weight of an N-(1,2-propanediol) fatty acid amide surfactant of the formula

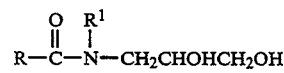

wherein R is a $C_7$–$C_{21}$ hydrocarbyl species (especially coconut, tallow, palm fatty alkyl and oleyl) and $R^1$ is a $C_1$–$C_6$ hydrocarbyl or substituted hydrocarbyl species, e.g., N-alkyl-N-(1,2-propanediol) fatty acid amides and N-hydroxyalkyl-N-(1,2-propanediol) fatty acid amides, especially N-methyl and N-hydroxyethyl;
(b) at least about 1% by weight of one or more non-amide detersive surfactants;
(c) from 0% to about 50% by weight of a detergency builder, preferably at least about 3% by weight of a non-phosphate builder;
(d) from 0% to about 5%, preferably at least about 0.1%, by weight of a detersive enzyme;
(e) from 0% to about 25% by weight of active adjunct materials; and
(f) the balance of the composition comprising moisture and carrier ingredients. Preferably, the compositions used for fabric laundering will contain at least about 5% by weight of a bleaching ingredient selected from bleaches and mixtures of bleaches with bleach activators.

In preferred compositions herein the non-amide detersive surfactant is a member selected from the group consisting of alkyl benzene sulfonate ("LAS") surfactants, alkyl sulfate ("AS") surfactants, alkyl ether sulfate ("AES") surfactants, amine oxide surfactants, ethoxylated alcohol surfactants, ethoxylated alkyl phenol surfactants, alkyl polyglucoside surfactants, fatty acid amides of polyhydroxyamines having 3 or more hydroxyl groups on a single carbon chain attached to said amine, fatty acid soap, and mixtures thereof. Preferred ratios of said N-alkyl-N-(1,2-propanediol) fatty acid amide:anionic surfactant are in the range of 1:3 to 3:1, preferably 1:1, by weight.

Another preferred composition herein contains a soil release polymer as the active adjunct material. Still other preferred compositions contain a member selected from the group consisting of sources of magnesium ions, sources of calcium ions, and mixtures thereof, as the active adjunct material. Such compositions are especially useful as high sudsing, grease removing hand-dishwashing compositions. Yet other preferred compositions additionally contain a fabric softening ingredient, especially clay and amine-cationic-smectite clay softener mixtures.

The invention also provides superior liquid detergent compositions which are especially useful for dishwashing, comprising:
(a) at least about 3% by weight of one or more anionic detersive surfactants;
(b) at least about 0.3% by weight of a source of magnesium ions, calcium ions, or mixtures thereof;
(c) at least about 3% by weight of an N-(1,2-propanediol) fatty acid amide surfactant of the formula

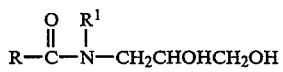

wherein R is a $C_7$–$C_{17}$ hydrocarbyl species and $R^1$ is selected from methyl, hydroxyethyl and mixtures thereof; and
(d) a liquid carrier. Such compositions can also, preferably, contain amine oxide, betaine and/or sultaine surfactants to boost suds and to enhance grease removal from tableware.

The invention also encompasses shampoo compositions containing various conditioners, anti-dandruff agents, and the like.

The invention also provides bar soap compositions characterized by their desirable hardness qualities and good sudsing.

The invention thus encompasses a method for cleaning soiled fabrics, comprising agitating said fabrics in an aqueous medium containing an effective amount (typically 10 ppm to at least about 2,000 ppm; effective for cleaning) of a composition as noted above. The invention also encompasses a method for cleaning soiled tableware, comprising contacting said tableware with an aqueous medium containing an effective amount (typically 10 ppm to at least about 1000 ppm; effective for cleaning) of a composition according to the above, especially with the aforesaid magnesium and/or calcium ions, under conditions of agitation.

All percentages, ratios and proportions herein are by weight, unless otherwise specified. All patents and other cited documents are incorporated herein by reference with respect to their technical disclosures.

DETAILED DESCRIPTION OF THE INVENTION

The N-(1,2-propanediol) fatty acid amides employed in the practice of this invention are provided by various reaction sequences, as illustrated by the following.

Sequence A:

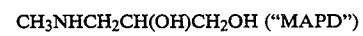

Sequence B:

Sequence A or B can be used when the alkyl substituent present on the amine reactant contains a hydroxyl group, e.g., monoethanolamine.

The amide surfactants used herein are then conveniently prepared by reacting the glycerol-amine prepared as noted above with a $C_8$–$C_{20}$ fatty acid ester (e.g., methyl, ethyl, etc. ester) typically in the presence of an alkoxide catalyst and alcohol and/or 1,2-propanediol solvent, as illustrated by the following.

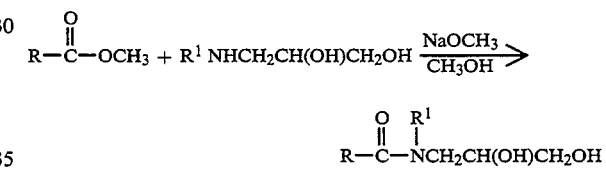

wherein R is typically $C_7$–$C_{21}$ alkyl or alkenyl and $R^1$ is typically $C_1$–$C_6$ alkyl, hydroxyalkyl, or alkenyl, preferably methyl (—$CH_3$) or hydroxyethyl (—$CH_2CH_2OH$). The examples hereinafter illustrate these reactions in greater detail.

Thus, the invention herein provides a novel and simple process for preparing the desired N-alkyl- or N-hydroxyalkyl-N-(1,2-propanediol) compounds by the reaction of glycidol with an N-alkylamine or N-hydroxyalkylamine, respectively, and the conversion thereof to the desired respective fatty acid amide surfactants by a reaction with a fatty acid ester.

In yet another mode, the preparation of the N-(1,2-propanediol) fatty acid amides can be conducted by reacting glyceraldehyde with an alkyl amine under hydrogen, with Ni catalyst, followed by reaction of the resulting N-alkyl-1,2-propanediol amine with a fatty ester in a solvent such as methanol or 1,2-propanediol solvent in the presence of a base catalyst such as sodium methoxide. A pressure reactor with a separate storage reservoir is typically employed. The reservoir (which can be pressurized) communicates with the reactor via suitable pipes, or the like. In use, a stirred slurry of a nickel catalyst (Raney Nickel 4200; Grace Chemicals) is first treated with hydrogen to remove traces of nickel oxides. This can be done in the reactor at about 50° C., 1,000 psig hydrogen. (If the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor. Thereafter, the glyceraldehyde is introduced from the storage reservoir into the reactor either under hydrogen pressure or by means of a high pressure pumping system, and the reaction is allowed to proceed at about 60°–85° C. and 2,000 psig hydrogen for about an hour. The progress of the reaction can be monitored by periodically removing samples of the reaction mixture and analyzing for reducibles using gas chromatography ("g.c."), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted). After removal of water, the N-alkyl-1,2 propanediol amine thus prepared is then admixed with a fatty acid methyl ester (e.g., coconutalkyl methyl ester) at a 1:1 mole ratio in 1,2-propanediol solvent and with sodium methoxide, and allowed to react for about 4 hours at 70° C. to provide the amide surfactant.

It is to be understood that the "active adjunct" materials used will vary, depending on the intended end-use of the final compositions. The following are intended only to be nonlimiting illustrations of such active adjuncts, more examples of which will readily come to mind of the skilled formulator.

Enzymes

Detersive enzymes can be included in the detergent formulations for a wide variety of purposes including removal of protein-based, carbohydrate-based, or triglyceride-based stains, for example, and prevention of refugee dye transfer. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 5 mg by weight, more typically about 0.05 mg to about 3 mg, of active enzyme per gram of the composition.

Suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo industries A/S under the registered trade name ESPERASE. The preparation of this enzyme and analogous enzymes is described in British Patent Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands).

Of interest in the category of proteolytic enzymes, especially for liquid detergent compositions, are enzymes referred to herein as Protease A and Protease B. Protease A and methods for its preparation are described in European Patent Application 130,756, published Jan. 9, 1985, incorporated herein by reference. Protease B is a proteolytic enzyme which differs from Protease A in that it has a leucine substituted for tyrosine in position 217 in its amino acid sequence. Protease B is described in European Patent Application Serial No. 87303761.8, filed Apr. 28, 1987, incorporated herein by reference. Methods for preparation of Protease B are also disclosed in European Patent Application 130,756, Bott et al, published Jan. 9, 1985, incorporated herein by reference.

Amylases include, for example, α-amylases obtained from a special strain of B. licheniforms, described in more detail in British Patent Specification No. 1,296,839 (Novo), previously incorporated herein by reference. Amylolytic proteins include, for example, RAPIDASE, International Bio-Synthetics, Inc. and TERMAMYL, Novo Industries.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, incorporated herein by reference, which discloses fungal cellulase produced from Humicola insolens. Suitable cellulases are also disclosed in GB-A-2.075.028; GB-A-2.095.275 and DE-OS-2.247.832.

Examples of such cellulases are cellulases produced by a strain of Humicola insolens (Humicola grisea var. thermoidea), particularly the Humicola strain DSM 1800, and cellulases produced by a fungus of Bacillus N or a cellulase 212-producing fungus belonging to the genus Aeromonas, and cellulase extracted from the hepatopancreas of a marine mollusc (Dolabella Auricula Solander).

Suitable lipase enzymes for detergent usage include those produced by microorganisms of the Pseudomonas group, such as Pseudomonas stutzeri ATCC 19.154, as disclosed in British Patent 1,372,034, incorporated herein by reference. Suitable lipases include those which show a positive immunoligical cross-reaction with the antibody of the lipase, produced by the microorganism *Pseudomonas fluorescens* IAH 1057. This lipase and a method for its purification have been described in Japanese Patent Application 53-20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Such lipases of the present invention should show a positive immunological cross reaction with the Amano-P antibody, using the standard and well-known immunodiffusion procedure according to Ouchterlony (Acta. Med. Scan., 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Psuedomonas nitroreducens* var. *lipolyticum* FERM P 1338 (available under the trade name Amano-CES), lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladoli*.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S, incorporated herein by reference.

A wide range of enzyme materials and means for their incorporation into synthetic detergent granules is also disclosed in U.S. Pat. No. 3,553,139, issued Jan. 5, 1971 to McCarty et al (incorporated herein by reference). Enzymes are further disclosed in U.S. Pat. No. 4,101,457, Place et al, issued Jul. 18, 1978, and in U.S. Pat. No. 4,507,219, Hughes, issued Mar. 26, 1985, both incorporated herein by reference. Enzyme materials useful for liquid detergent formulations, and their incorporation into such formulations, are disclosed in U.S. Pat. No. 4,261,868, Hora et al, issued Apr. 14, 1981, also incorporated herein by reference.

For granular detergents, the enzymes are preferably coated or prilled with additives inert toward the enzymes to minimize dust formation and improve storage stability. Techniques for accomplishing this are well known in the art. In liquid formulations, an enzyme stabilization system is preferably utilized. Enzyme stabilization techniques for aqueous detergent compositions are well known in the art. For example, one technique for enzyme stabilization in aqueous solutions involves the use of free calcium ions from sources such as calcium acetate, calcium formate, and calcium propionate. Calcium ions can be used in combination with short chain carboxylic acid salts, perferably formates. See, for example, U.S. Pat. No. 4,318,818, Letton, et al, issued Mar. 9, 1982, incorporated herein by reference. It has also been proposed to use polyols like glycerol and sorbitol. Alkoxy-alcohols, dialkylglycoethers, mixtures of polyvalent alcohols with polyfunctional aliphatic amines (e.g., such as diethanolamine, triethanolamine, di-isopropanolamine, etc.), and boric acid or alkali metal borate. Enzyme stabilization techniques are additionally disclosed and exemplified in U.S. Pat. No. 4,261,868, issued Apr. 14, 1981 to Horn, et al., U.S. Pat. No. 3,600,319, issued Aug. 17, 1971 to Gedge, et al., both incorporated herein by reference, and European Patent Application Publication No. 0 199 405, Application No. 86200586.5, published Oct. 29, 1986, Venegas. Non-boric acid and borate stabilizers are preferred. Enzyme stabilization systems are also described, for example, in U.S. Pat. Nos. 4,261,868, 3,600,319, and 3,519,570.

Surfactants

Typically, the laundry and dishwashing compositions herein will comparise from about 3% to about 40% by weight of detersive surfactants. One type of anionic surfactant which can be utilized encompasses alkyl ester sulfonates. The preferred alkyl ester sulfonate surfactant, especially for laundry applications, comprise alkyl ester sulfonate surfactants of the structural formula:

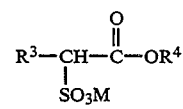

wherein $R^3$ is a $C_8-C_{20}$ hydrocarbyl, preferably an alkyl, or combination thereof, $R^4$ is a $C_1-C_6$ hydrocarbyl, preferably an alkyl, or combination thereof, and M is a soluble salt-forming cation, such as sodium, potassium, and lithium salts, and substituted or unsubstituted ammonium salts, such as methyl-, dimethyl, -trimethyl, and quaternary ammonium cations, e.g., tetramethylammonium and dimethyl piperdinium, and cations derived from alkanolamines, e.g., monoethanolamine, diethanolamine, and triethanolamine. Preferably, $R^3$ is $C_{10}-C_{16}$ alkyl, and $R^4$ is methyl, ethyl or isopropyl. Especially preferred are the methyl ester sulfonates wherein $R^3$ is $C_{14}-C_{16}$ alkyl.

Alkyl sulfate surfactants are another type of anionic surfactant for use herein. In addition to providing excellent overall cleaning ability when used in combination with the N-(1,2-propanediol) fatty acid amides, including good grease/oil cleaning over a wide range of temperatures, wash concentrations, and wash times, dissolution of alkyl sulfates can be obtained, as well as improved formulability in liquid detergent formulations are water soluble salts or acids of the formula $ROSO_3M$ wherein R preferably is a $C_{10}-C_{24}$ hydrocarbyl, preferably an alkyl or hydroxyalkyl having a $C_{10}-C_{20}$ alkyl component, more preferably a $C_{12}-C_{18}$ alkyl or hydroxyalkyl, and M is H or a cation, as noted above. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated (ether) sulfate ("AES") surfactants are another category of useful anionic surfactant. These surfactants are water soluble salts or acids typically of the formula $RO(A)_mSO_3M$ wherein R is an unsubstituted $C_{10}-C_{24}$ alkyl component, preferably a $C_{12}-C_{12}$ alkyl, more preferably $C_{12}-C_{18}$ alkyl, A is an ethoxy or propoxy unit, m is greater than zero, typically between about 0.5. and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanol amines, e.g. monoethanol amine, diethanol amine, and triethanol amine, and mixtures thereof. Exemplary surfactants are $C_{12}-C_{18}$ alkyl polyethoxylate (1.0) sulfate, $C_{12}-C_{18}$ alkyl polyethoxylate (2.25) sulfate, $C_{12}-C_{18}$ alkyl polyethoxylate (3.0) sulfate, and $C_{12}-C_{18}$ alkyl polyethoxylate (4.0) sulfate wherein M is conveniently selected from sodium and potassium.

Other anionic surfactants useful for detersive purposes can also be included in the compositions hereof. These can include salts (including, for example, sodium, potassium, ammonium, and substituted ammonium salts such as mono-, di- and triethanolamine salts) of soap, $C_9-C_{20}$ linear alkylbenzenesulfonates, $C_8-C_{22}$ primary or secondary alkanesulfonates, sulfonated polycarboxylic acids prepared by sulfonation of the pyrolyzed product of alkaline earth metal citrates, e.g., as described in British Patent Specification No. 1,082,179, alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl tautares, fatty acid amides of methyl tauride, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO^-M^+$ wherein R is a $C_8$–$C_{22}$ alkyl, k is an integer from 0 to 10, and M is a soluble salt-forming cation, and fatty acids esterified with isethionic acid and neutralized with sodium hydroxide. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin et al., at Column 23, line 58 through Column 29, line 23.

Nonionic Detergent Surfactants

Suitable nonionic detergent surfactants are generally disclosed in U.S. Pat. No. 3,929,678, Laughlin et al., issued Dec. 30, 1975, at column 13, line 14 through column 16, line 6. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include IGEPAL CO-630, marketed by the GAF Corporation; and TRITON X-45, X-114, X-100, and X-102, all marketed by the Rohm & Haas Company. These compounds are commonly referred to as alkyl phenol alkoxylates, (e.g., alkyl phenol ethoxylates).

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include TERGITOL 15-S-9 (the condensation product of $C_{11}$–$C_{15}$ linear secondary alcohol with 9 moles ethylene oxide), TERGITOL 24-L-6 NMW (the condensation product of $C_{12}$–$C_{14}$ primary alcohol with 6 moles ethylene oxide with a narrow molecular weight distribution), both marketed by Union Carbide Corporation; NEODOL 45-9 (the condensation product of $C_{14}$–$C_{15}$ linear alcohol with 9 moles of ethylene oxide), NEODOL 23-6.5 (the condensation product of $C_{12}$–$C_{13}$ linear alcohol with 6.5 moles of ethylene oxide), NEODOL 45-7 (the condensation product of $C_{14}$–$C_{15}$ linear alcohol with 7 moles of ethylene oxide), NEODOL 45-4 (the condensation product of $C_{14}$–$C_{13}$ linear alcohol with 4 moles of ethylene oxide), marketed by Shell Chemical Company, and KYRO EOB (the condensation product of $C_{13}$–$C_{15}$ alcohol with 9 moles ethylene oxide), marketed by The Procter & Gamble Company. This category of nonionic surfactant is referred to generally as "alkyl ethoxylates."

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available PLURONIC surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available TETRONIC compounds, marketed by BASF.

5. Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula $$R^3(OR^4)_xN(R^5)_2$$
$$\overset{\parallel}{O}$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri -, tetra-, and pentaglucosides and tallow alkyl tetra-, penta-, and hexaglucosides.

The preferred alkylpolyglycolysides have the formula

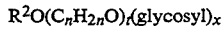

$$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. Fatty acid amide surfactants having the formula:

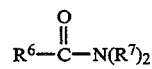

$$R^6-\overset{O}{\underset{\|}{C}}-N(R^7)_2$$

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3.

Preferred amides are $C_8$–$C_{20}$ ammonia amides, monoethanolamides, diethanolamides, and isopropanolamides.

Cationic Surfactants

Cationic detersive surfactants can also be included in detergent compositions of the present invention. Cationic surfactants include the ammonium surfactants such as alkyldimethylammonium halogenides, and those surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl, ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Other cationic surfactants useful herein are also described in U.S. Pat. No. 4,228,044, Cambre, issued Oct. 14, 1980, incorporated herein by reference.

Other Surfactants

Ampholytic surfactants can be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight chain or branched. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 to Laughlin et al., issued Dec. 30, 1975 at column 19, lines 18–35 (herein incorporated by reference) for examples of ampholytic surfactants.

Zwitterionic surfactants can also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 (herein incorporated by reference) for examples of zwitterionic surfactants.

Ampholytic and zwitterionic surfactants are generally used in combination with one or more anionic and/or nonionic surfactants.

In addition to enzymes, the N-(1,2-propanediol) fatty acid amide, and any optional deterslye surfactants, the detergents hereof can include one or more other detergent adjunct materials or other materials for assisting in or enhancing cleaning performance, treatment of the substrate to be cleaned, or modify the aesthetics of the detergent composite or modify the (e.g., perfumes, colorants, dyes, etc.).

Builders

Detergent builders can optionally be included in the compositions hereof to assist in controlling mineral hardness. Inorganic as well as organic builders can be used.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates, including sodium carbonate and sesquicarbonate and mixtures thereof with ultra-fine calcium carbonate as disclosed in German Patent Application No. 2,321,001 published on Nov. 15, 1973, the disclosure of which is incorporated herein by reference.

Aluminosilicate builders are especially useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$M_z(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred aluminosilicates are zeolite builders which have the formula:

$$Na_z[(AlO_2)_z(SiO_2)_y] \cdot xH_2O$$

wherein z and y are integers of at least 6, the molar ratio of z to y is in the range from 1.0 to about 0.5, and x is an integer from about 15 to about 264.

Useful aluminostlicate ion exchange materials are commercially available. These aluminosilicates can be crystalline or amorphous in structure and can be naturally-occurring aluminosilicates or synthetically derived. A method for producing aluminosilicate ion exchange materials as disclosed in U.S. Pat. No. 3,985,669, Krummel, et al., issued Oct. 12, 1976, incorporated herein by reference. Preferred synthetic crystalline aluminostlicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Preferably, the aluminosilicate has a particle size of about 0.1-10 microns in diameter.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Examples of phosphonate builder salts are the water-soluble salts of ethane 1-hydroxy-1, 1-diphosphonate particularly the sodium and potassium salts, the water-soluble salts of methylene diphosphonic acid e.g. the trisodium and tripotassium salts and the water-soluble salts of substituted methylene diphosphonic acids, such as the trisodium and tripotassium ethylidene, isopyropylidene benzylmethylidene and halo methylidene phosphonates. Phosphonate builder salts of the aforementioned types are disclosed in U.S. Pat. Nos. 3,159,581 and 3,213,030 issued Dec. 1, 1964 and Oct. 19, 1965, to Diehl; U.S. Pat. No. 3,422,021 issued Jan. 14, 1969, to Roy; and U.S. Pat. Nos. 3,400,148 and 3,422,137 issued Sep. 3, 1968, and Jan. 14, 1969 to Quimby, said disclosures being incorporated herein by reference.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al, U.S. Pat. No. 3,635,830, issued Jan. 18, 1972, both of which are incorporated herein by reference.

A specific type of ether polycarboxylates useful as builders in the present invention also include those having the general formula:

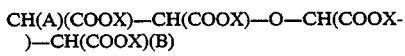

wherein A is H or OH; B is H or —O—CH(COOX)—CH$_2$(COOX); and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is —O—CH(COOX)—CH$_2$(COOX), then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al, on May 5, 1987.

Suitable ether polycarboxylates also include cyclic compounds, particularly alicyclic compounds, such as those described in U.S. Pat. No. 3,923,679; 3,835,163; 4,158,635; 4,120,874 and 4,102,903, all of which are incorporated herein by reference.

Other useful detergency builders include the ether hydroxypolycarboxylates represented by the structure:

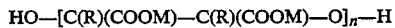

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Still other ether polycarboxylates include copolymers of maleic anhydride with ethylene or vinyl methyl ether, 1, 3, 5-trihydroxy benzene-2, 4, 6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations, but can also be used in granular compositions.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Useful succinic acid builders include the $C_5$–$C_{20}$ alkyl succinic acids and salts thereof. A particularly preferred compound of this type is dodecenylsuccinic acid. Alkyl succinic acids typically are of the general formula R—CH(COOH)CH$_2$(COOH) i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristyl succinate, palmiryl succinate, 2-dodecenyl succinate (preferred), 2-pentadecenylsuccinate, and the like. Laurylsuccinares are the preferred builders of this group, and are described in European Patent Application 86200690.5/0,200,263, published Nov. 5, 1986.

Examples of useful builders also include sodium and potassium carboxymethyl oxymalonate, carboxymethyl oxysuccinate, cis-cyclohexanehexacarboxylate, cis-cyclopentane-tetracarboxylate, water-soluble polyacrylates (these polyacrylates having molecular weights to above about 2,000 can also be effectively utilized as dispersants), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citracenic acid and methylenemalonic acid.

Other organic builders known in the art can also be used. For example, monocarboxylic acids, and soluble salts thereof, having long chain hydrocarbyls can be utilized. These would include materials generally referred to as "soaps." Chain lengths of $C_{10}$–$C_{20}$ are typically utilized. The hydrocarbyls can be saturated or unsaturated.

Bleaching Compounds—Bleaching Agents and Bleach Activators

The detergent compositions herein may contain bleaching agents or bleaching compositions containing bleaching agent and one or more bleach activators. When present bleaching compounds will typically be present at levels of from about 1% to about 20%, more typically from about 1% to about 10%, of the detergent composition. In general, bleaching compounds are optional components in non-liquid formulations, e.g., granular detergents. If present, the amount of bleach activators will typically be from about 0.1% to about 60%, more typically from about 0.5% to about 40% of the bleaching composition.

The bleaching agents used herein can be any of the bleaching agents useful for detergent compositions in textile cleaning, hard surface cleaning, or other cleaning purposes that are now known or become known. These include oxygen bleaches as well as other bleaching agents. In contrast with certain polyol surfactants, the N-(1,2-propanediol) fatty acid amide surfactants herein are compatible with perborate bleach, such as sodium perborate tetrahydrate and sodium perborate monohydrate.

Another category of bleaching agent that can be used encompasses percarboxylic ("percarbonate") acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burns et al., filed Jun. 3, 1985, European Patent Application 0,133,354, Banks et al., published Feb. 20, 1985, and U.S. Pat. No. 4,412,934, Chung et al., issued Nov. 1, 1983, all of which are incorporated by reference herein. Highly preferred bleaching agents also include 6-nonylamino-6-oxoperoxycaproic acid as described in U.S. Pat. No. 4,634,551, issued Jan. 6, 1987 to Burns, et al, incorporated herein by reference.

Peroxygen bleaching agents can also be used. Suitable peroxygen bleaching compounds include sodium carbonate peroxyhydrate, sodium pyrophosphate peroxyhydrate, urea peroxyhydrate, and sodium peroxide. Persulfate bleach (e.g., OXONE, manufactured commercially by DuPont) can also be used.

Mixtures of bleaching agents can also be used.

Peroxygen bleaching agents are preferably combined with bleach activators, which lead to the in situ production in aqueous solution (i.e., during the washing process) of the peroxy acid corresponding to the bleach activator.

Preferred bleach activators incorporated into compositions of the present invention have the general formula:

wherein R is an alkyl group containing from about 1 to about 18 carbon atoms wherein the longest linear alkyl chain extending from and including the carbonyl carbon contains from about 6 to about 10 carbon atoms and L is a leaving group, the conjugate acid of which has a PKa in the range of from about 4 to about 13. These bleach activators are described in U.S. Pat. No. 4,915,854, issued Apr. 10, 1990 to Hao, et al., incorporated herein by reference, and U.S. Pat. No. 4,412,934, which was previously incorporated herein by reference.

Bleaching agents other than oxygen bleaching agents are also known in the art and can be utilized herein. One type of nonoxygen bleaching agent of particular interest includes photo-activated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanines and a photoactivated bleaching process are described in U.S. Pat. No. 4,033,718, issued Jul. 5, 1977 to Holcombe et al., incorporated herein by reference. Typically, detergent compositions will contain about 0.025% to about 1.25%, by weight, of sulfonated zinc phthalocyanine.

Polymeric Soil Release Agent

Any polymeric soil release agents known to those skilled in the art can be employed in the practice of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

Whereas it can be beneficial to utilize polymeric soil release agents in any of the detergent compositions hereof, especially those compositions utilized for laundry or other applications wherein removal of grease and oil from hydrophobic surfaces is needed, the presence of N-(1,2-propanediol) fatty acid amide in detergent compositions also containing anionic surfactants can enhance performance of many of the more commonly utilized types of polymeric soil release agents. Anionic surfactants interfere with the ability of certain soil release agents to deposit upon and adhere to hydrophobic surfaces. These polymeric soil release agents have nonionic hydrophile segments or hydrophobe segments which are anionic surfactant-interactive.

The compositions hereof for which improved polymeric soil release agent performance can be obtained through the use of N-(1,2-propanediol) fatty acid amide are those which contain an anionic surfactant system, an artionic surfactant-interactive soil release agent and a soil release agent-enhancing amount of the N-(1,2-propanediol) fatty acid amide, wherein: (I) anionic surfactant-interaction between the soil release agent and the anionic surfactant system of the detergent composition can be shown by a comparison of the level of soil release agent (SRA) deposition on hydrophobic fibers (e.g., polyester) in aqueous solution between (A) a "Control" run wherein deposition of the SRA of the detergent composition in aqueous solution, in the absence of the other detergent ingredients, is measured, and (B) an "SRA/Anionic surfactant" test run wherein the same type and amount of the anionic surfactant system utilized in detergent composition is combined in aqueous solution with the SRA, at the same weight ratio of SRA to the anionic surfactant system of the detergent composition, whereby reduced deposition in (B) relative to (A) indicates anionic-surfactant interaction; and (II) whether the detergent composition contains a soil release agent-enhancing amount of N-(1,2-propanediol) fatty acid amide can be determined by a comparison of the SRA deposition of the SRA/Anionic surfactant test run of (B) with soil release agent deposition in (C) an "SRA/Anionic surfactant/PFA test run" wherein the same type and level of N-(1,2-propanediol) fatty acid amide of the detergent composition is combined with the soil release agent and anionic surfactant system corresponding to said SRA/anionic surfactant test run, whereby improved deposition of the soil release agent in test run (C) relative to test run (B) indicates that a soil release agent-enhancing amount of N-(1,2-propanediol) fatty acid amide is present. For purposes hereof, the tests hereof should be conducted at anionic surfactant concentrations in the aqueous solution that are above the critical micelle concentration (CMC) of the anionic surfactant and preferably above about 100 ppm. The polymeric soil release agent concentration should be at least 15 ppm. A swatch of polyester fabric should be used for the hydrophobic fiber source. Identical swatches are immersed and agitated in 35° C. aqueous solutions for the respective test runs for a period of 12 minutes, then removed, and analyzed. Polymeric soil release agent deposition level can be determined by radiotagging the soil release agent prior to treatment and subsequently conducting radiochemical analysis, according to techniques known in the art.

As an alternative to the radiochemical analytical methodology discussed above, soil release agent deposition can alternately be determined in the above test runs (i.e., test runs A, B, and C) by determination of ultraviolet light (UV) absorbance of the test solutions, according to techniques well known in the art. Decreased UV absorbance in the test solution after removal of the hydrophobic fiber material corresponds to increased SRA deposition. As will be understood by those skilled in the art, UV analysis should not be utilized for test solutions containing types and levels of materials which cause excessive UV absorbance interference, such as high levels of surfactants with aromatic groups (e.g., alkyl benzene sulfonates, etc.).

Thus by "soil release agent-enhancing amount" of N-(1,2-propanediol) fatty acid amide is meant an amount of such surfactant that will enhance deposition of the soil release agent upon hydrophobic fibers, as described above, or an amount for which enhanced grease/oil cleaning performance can be obtained for fabrics washed in the detergent composition hereof in the next subsequent cleaning operation.

The amount of N-(1,2-propanediol) fatty acid amide needed to enhance deposition will vary with the anionic surfactant selected, the amount of anionic surfactant, the particular soil release agent chosen, as well as the particular N-(1,2-propanediol) fatty acid amide chosen. Generally, compositions will comprise from about 0.01% to about 10%, by weight, of the polymeric soil release agent, typically from about 0.1% to about 5%, and from about 4% to about 50%, more typically from about 5% to about 30% of anionic surfactant. Such compositions should generally contain at least about 1%, preferably at least about 3%, by weight, of the N-(1,2-propanediol) fatty acid amide, though it is not intended to necessarily be limited thereto.

The polymeric soil release agents for which performance is enhanced by N-(1,2-propanediol) fatty acid amide in the presence of anionic surfactant include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures thereof, (iii) poly (vinyl ester) segments, preferably poly(vinyl acetate), having a degree of polymerization of at least 2, or (iv) $C_1$–$C_4$ alkyl ether or $C_4$ hydroxyalkyl ether substituents, or mixtures thereof, wherein said substituents are present in the form of $C_1$–$C_4$ alkyl ether or $C_4$ hydroxyalkyl ether cellulose derivatives, or mixtures thereof, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from 2 to about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink, incorporated herein by reference.

Polymeric soil release agents useful in the present invention include cellulosic derivatives such as hydroxyether cellulosic polymers, copolymeric blocks of ethylene terephthalate or propylene terephthalate with polyethylene oxide or polypropylene oxide terephthalate, and the like.

Cellulosic derivatives that are functional as soil release agents are commercially available and include hydroxyethers of cellulose such as Methocel® (Dow).

Cellulosic soil release agents for use herein also include those selected from the group consisting of $C_1$–$C_4$ alkyl and $C_4$ hydroxyalkyl cellulose such as methyl cellulose, ethyl cellulose, hydroxypropyl methyl cellulose, and hydroxybutyl methyl cellulose. A variety of cellulose derivatives useful as soil release polymers are disclosed in U.S. Pat. No. 4,000,093, issued Dec. 28, 1976 to Nicol, et al, incorporated herein by reference.

Soil release agents characterized by poly(vinyl ester) hydrophobe segments include graft copolymers of poly(vinyl ester), e.g., $C_1$–$C_6$ vinyl esters, preferably poly(vinyl acetate) grafted onto polyalkylene oxide backbones, such as polyethylene oxide backbones. Such materials are known in the art and are described in European Patent Application 0 219 048, published Apr.

22, 1987 by Kud, et al. Suitable commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. More specifically, these polymers are comprised of repeating units of ethylene terephthalate and PEO terephthalate in a mole ratio of ethylene terephthalate units to PEO terephthalate units of from about 25:75 to about 35:65, said PEO terephthalate units containing polyethylene oxide having molecular weights of from about 300 to about 2000. The molecular weight of this polymeric soil release agent is in the range of from about 25,000 to about 55,000. See U.S. Pat. No. 3,959,230 to Hays, issued May 25, 1976, which is incorporated by reference. See also U.S. Pat. No. 3,893,929 to Basadur issued Jul. 8, 1975 (incorporated by reference) which discloses similar copolymers.

Another preferred polymeric soil release agent is a polyester with repeat units of ethylene terephthalate units containing 10–15% by weight of ethylene terephthalate units together with 90–80% by weight of polyoxyethylene terephthalate units, derived from a polyoxyethylene glycol of average molecular weight 300–5,000, and the mole ratio of ethylene terephthalate units to polyoxyethylene terephthalate units in the polymeric compound is between 2:1 and 6:1. Examples of this polymer include the commercially available material ZELCON 5126 (from Dupont) and MILEASE T (from ICI). These polymers and methods of their preparation are more fully described in U.S. Pat. No. 4,702,857, issued Oct. 27, 1987 to Gosselink, which is incorporated herein by reference.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone, said soil release agent being derived from allyl alcohol ethoxylate, dimethyl terephthalate, and 1,2 propylene diol, wherein after sulfonation, the terminal moieties of each oligomer have, on average, a total of from about 1 to about 4 sulfonate groups. These soil release agents are described fully in U.S. Pat. No. 4,968,451, issued Nov. 6, 1990 to J. J. Scheibel and E. P. Gosselink, incorporated herein by reference.

Other suitable polymeric soil release agents include the ethyl- or methyl-capped 1,2-propylene terephthalate polyoxyethylene terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, wherein the anionic end-caps comprise sulfo-polyethoxy groups derived from polyethylene glycol (PEG), the block polyester oligomeric compounds of U.S. Pat. No. 4,702,857, issued Oct. 27, 1987 to Gosselink, having polyethoxy end-caps of the formula X—(OCH$_2$CH$_2$)$_n$— wherein n is from 12 to about 43 and X is a C$_1$–C$_4$ alkyl, or preferably methyl, all of these patents being incorporated herein by reference.

Additional polymeric soil release agents include the soil release agents of U.S. Pat. No. 4,877,896, issued Oct. 31, 1989 to Maldonado et al., which discloses anionic, especially sulfoaroyl, end-capped terephthalate esters, said patent being incorporated herein by reference. The terephthalate esters contain unsymmetrically substituted oxy-1,2-alkyleneoxy units. Included among the soil release polymers of U.S. Pat. No. 4,877,896 are materials with polyoxyethylene hydrophile components or C$_3$ oxyalkylene terephthalate (propylene terephthalate) repeat units within the scope of the hydrophobe components of (b)(i) above. It is the polymeric soil release agents characterized by either, or both, of these criteria that particularly benefit from the inclusion of the N-(1,2-propanediol) fatty acid amides hereof, in the presence of anionic surfactants.

If utilized, soil release agents will generally comprise from about 0.01% to about 10.0%, by weight, of the detergent compositions herein, typically from about 0.1% to about 5%, preferably from about 0.2% to about 3.0%.

Chelating Agents

The detergent compositions herein may also optionally contain one or more iron and manganese chelating agents as a builder adjunct material. Such chelating agents can be selected from the group consisting of amino carboxylates, amino phosphonates, polyfunctionally-substituted aromatic chelating agents and mixtures thereof, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents in compositions of the invention can have one or more, preferably at least two, units of the substructure

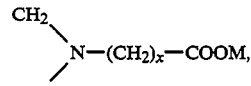

wherein M is hydrogen, alkali metal, ammonium or substituted ammonium (e.g. ethanolamine) and x is from 1 to about 3, preferably 1. Preferably, these amino carboxylates do not contain alkyl or alkenyl groups with more than about 6 carbon atoms. Operable amine carboxylates include ethylenediaminetetraacetates, N-hydroxyethylethylenediaminetriacetates, nitrilotriacetates, ethylenediamine tetraproprionates, triethylenetetraaminehexaacetates, diethylenetriaminepentaacetates, and ethanoldiglycines, alkali metal, ammonium, and substituted ammonium salts thereof and mixtures thereof.

Amino phosphonates are also suitable for use as chelating agents in the compositions of the invention when at least low levels of total phosphorus are permitted in detergent compositions. Compounds with one or more, preferably at least two, units of the substructure

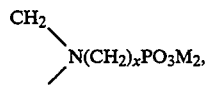

wherein M is hydrogen, alkali metal, ammonium or substituted ammonium and x is from I to about 3, preferably 1, are useful and include ethylenediaminetetrakis (methylenephosphonates), nitrilotris (methylenephosphonates) and diethylenetriaminepentakis (methylenephosphonates). Preferably, these amino phosphonates do not contain alkyl or alkenyl groups with more than about 6 carbon atoms. Alkylene groups can be shared by substructures.

Polyfunctionally-substituted aromatic chelating agents are also useful in the compositions herein. These materials can comprise compounds having the general formula

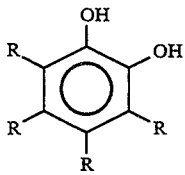

wherein at least one R is —SO$_3$H or —COOH or soluble salts thereof and mixtures thereof. U.S. Pat. No. 3,812,044, issued May 21, 1974, to Connor et al, incorporated herein by reference, discloses polyfunctionally-substituted aromatic chelating and sequestering agents. Preferred compounds of this type in acid form are dihydroxydisulfobenzenes such as 1,2-dihydroxy-3,5-disulfobenzene. Alkaline detergent compositions can contain these materials in the form of alkali metal, ammonium or substituted ammonium (e.g. mono- or triethanol-amine) salts.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Clay Soil Removal/Anti-redeposition Agents

The compositions of the present invention can also optionally contain water-soluble ethoxylated amines having clay soil removal and anti-redeposition properties. Granular detergent compositions which contain these compounds typically contain from about 0.01% to about 10.0% by weight of the water-soluble ethoxylated amines; liquid detergent compositions, typically about 0.01% to about 5%. These compounds are selected preferably from the group consisting of:

(1) ethoxylated monoamines having the formula:

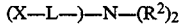

(2) ethoxylated diamines having the formula:

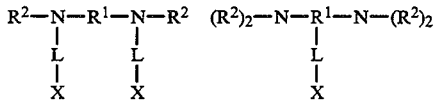

or

(3) ethoxylated polyamines having the formula:

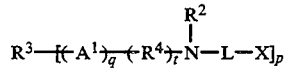

(4) ethoxylated amine polymers having the general formula:

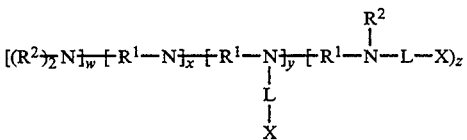

and (5) mixtures thereof; wherein A$^1$ is

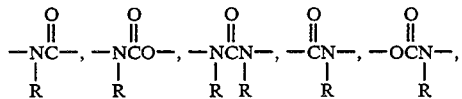

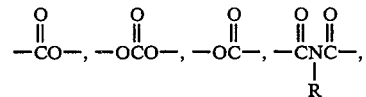

or —O—; R is H or C$_1$–C$_4$ alkyl or hydroxyalkyl; R$^1$ is C$_2$–C$_{12}$ alkylene, hydroxyalkylene, alkenylene, arylene or alkarylene, or a C$_2$–C$_3$ oxyalkylene moiety having from 2 to about 20 oxyalkylene units provided that no O—N bonds are formed; each R$^2$ is C$_1$–C$_4$ or hydroxyalkyl, the moiety —L—X, or two R$^2$ together form the moiety —(CH$_2$)$_r$—, —A$^2$—(CH$_2$)$_s$—, wherein A$^2$ is —O— or —CH$_2$—, r is 1 or 2, s is 1 or 2, and r+s is 3 or 4; X is a nonionic group, an anionic group or mixture thereof; R$^3$ is a substituted C$_3$–C$_{12}$ alkyl, hydroxyalkyl, alkenyl, aryl, or alkaryl group having substitution sites; R$^4$ is C$_1$–C$_{12}$ alkylene, hydroxyalkylene, alkenylene, arylene or alkarylene, or a C$_1$–C$_3$ oxyalkylene moiety having from 2 to about 20 oxyalkylene units provided that no O—O or O—N bonds are formed; L is a hydrophilic chain which contains the polyoxyalkylene moiety —[(R$^5$O)$_m$(CH$_2$CH$_2$O)$_n$]—, wherein R$^5$ is C$_1$–C$_4$ alkylene or hydroxyalkylene and m and n are numbers such that the moiety —(CH$_2$CH$_2$O)$_n$— comprises at least about 50% by weight of said polyoxyalkylene moiety; for said monoamines, m is from 0 to about 4, and n is at least about 12; for said diamines, m is from 0 to about 3, and n is at least about 6 when R$^1$ is C$_2$–C$_3$ alkylene, hydroxyalkylene, or alkenylene, and at least about 3 when R$^1$ is other than C$_2$–C$_3$ alkylene, hydroxyalkylene or alkenylene; for said polyamines and amine polymers, m is from 0 to about 10 and n is at least about 3; p is from 3 to 8; q is 1 or 0; t is 1 or 0, provided that t is 1 when q is 1; w is 1 or 0; x+y+z is at least 2; and y+z is at least 2. The most preferred soil release and anti-redeposition agent is ethoxylated tetraethylenepentamine. Exemplary ethoxylated amines are further described in U.S. Pat. No. 4,597,898, VanderMeer, issued Jul. 1, 1986, incorporated herein by reference. Another group of preferred clay soil removal/antiredeposition agents are the cationic compounds disclosed in European Patent Application 111,965, Oh and Gosselink, published Jun. 27, 1984, incorporated herein by reference. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985, all of which are incorporated herein by reference.

Other clay soil removal and/or anti redeposition agents known in the art can also be utilized in the compositions hereof. Another type of preferred anti-redeposition agent includes the carboxy methyl cellulose (CMC) materials. These materials are well known in the art.

Polymeric Dispersing Agents

Polymeric dispersing agents can advantageously be utilized at levels from about 0.1% to about 7%, by weight, in the compositions hereof. These materials can aid in calcium and magnesium hardness control. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polycarboxylate materials which can be employed as the polymeric dispersing agent herein are these polymers or copolymers which contain at least about 60% by weight of segments with the general formula

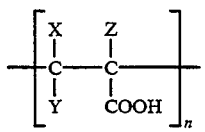

wherein X, Y, and Z are each selected from the group consisting of hydrogen, methyl, carboxy, carboxymethyl, hydroxy and hydroxymethyl; a salt-forming cation and n is from about 30 to about 400. Preferably, X is hydrogen or hydroxy, Y is hydrogen or carboxy, Z is hydrogen and M is hydrogen, alkali metal, ammonia or substituted ammonium.

Polymeric polycarboxylate materials of this type can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, iraconic acid, aconitic acid, mesaconic acid, citraconic acid and methylenemalonic acid. The presence in the polymeric polycarboxylates herein of monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967. This patent is incorporated herein by reference.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, which publication Is incorporated herein by reference.

Another polmeric material which can be included is polyethylene glycol (PEG). PEG can exhibit dispersing agent performance as well as act as a clay soil removal-/antiredeposition agent. Typical molecular weight ranges for these purposes range from about 500 to about 100,000, preferably from about 1,000 to about 50,000, more preferably from about 1,500 to about 10,000.

Brightener

Any optical brighteners or other brightening or whitening agents known in the art can be incorporated at levels typically from about 0.05% to about 1.2%, by weight, into the detergent compositions hereof.

The choice of brightener for use in detergent compositions will depend upon a number of factors, such as the type of detergent, the nature of other components present in the detergent composition, the temperatures of wash water, the degree of agitation, and the ratio of the material washed to tub size.

The brightener selection is also dependent upon the type of material to be cleaned, e.g., cottons, synthetics, etc. Since most laundry detergent products are used to clean a variety of fabrics, the detergent compositions should contain a mixture of brighteners which will be effective for a variety of fabrics. It is of course necessary that the individual components of such a brightener mixture be compatible.

Commercial optical brighteners which may be useful in the present invention can be classified into subgroups which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present invention include, but are not necessarily limited to, derivatives of bis(triazinyl)amino-stilbene; bisacylamino derivatives of stilbene; triazole derivatives of stilbene; oxadiazole derivatives of stilbene; oxazole derivatives of stilbene; and styryl derivatives of stilbene.

Certain derivatives of bis(triazinyl)aminostilbene which may be useful in the present invention may be prepared from 4,4'-diamine-stilbene-2,2'-disulfonic acid.

Coumarin derivatives which may be useful in the present invention include, but are not necessarily limited to, derivatives substituted in the 3-position, in the 7-position, and in the 3- and 7-positions.

Carboxylic acid derivatives which may be useful in the present invention include, but are not necessarily limited to, fumaric acid derivatives; benzoic acid derivatives; p-phenylene-bis-acrylic acid derivatives; naphthalenedicarboxylic acid derivatives; heterocyclic acid derivatives; and cinnamic acid derivatives.

Cinnamic acid derivatives which may be useful in the present invention can be further subclassified into groups which include, but are not necessarily limited to, cinnamic acid derivatives, styrylazoles, styrylbenzofurans, styryloxadiazoles, styryltriazoles, and styrylpolyphenyls, as disclosed on page 77 of the Zahradnik reference.

The styrylazoles can be further subclassified into styrylbenzoxazoles, styrylimidazoles and styrylthiazoles, as disclosed on page 78 of the Zahradnik reference. It will be understood that these three identified subclasses may not necessarily reflect an exhaustive list of subgroups into which styrylazoles may be subclassified.

Another class of optical brighteners which may be useful in the present invention are the derivatives of dibenzothiophene-5,5-dioxide disclosed at page 741-749 of *The Kirk-Othmer Encyclopedia of Chemical Technology*, Volume 3, pages 737-750 (John Wiley & Son, Inc., 1962), the disclosure of which is incorporated herein by reference, and include 3,7-diaminodibenzothiophene-2,8-disulfonic acid 5,5 dioxide.

Another class of optical brighteners which may be useful in the present invention include azoles, which are derivatives of 5-membered ring heterocycles. These can be further subcategorized into monoazoles and bisazoles. Examples of monoazoles and bisazoles are disclosed in the *Kirk-Othmer* reference.

Another class of brighteners which may be useful in the present invention are the derivatives of 6-membered-ring heterocycles disclosed in the *Kirk-Othmer* reference. Examples of such compounds include brighteners derived from pyrazine and brighteners derived from 4-aminonaphthalamide.

In addition to the brighteners already described, miscellaneous agents may also be useful as brighteners. Examples of such miscellaneous agents are disclosed at pages 93-95 of the Zahradnik reference, and include 1-hydroxy-3,6,8-pyrenetrisulphonic acid; 2,4-dimethoxy-1,3,5-triazin-6-yl-pyrene; 4,5-diphenylimidazolonedisulphonic acid; and derivatives of pyrazolinequinoline.

Other specific examples of optical brighteners which may be useful in the present invention are those identified in U.S. Pat. No. 4,790,856, issued to Wixon on Dec. 13, 1988, the disclosure of which is incorporated herein by reference. These brighteners include the PHORWHITE series of brighteners from Verona. Other brighteners disclosed in this reference include: Tinopal UNPA, Tinopal CBS and Tinopal 5BM; available from Ciba-Geigy; Arctic White CC and Attic White CWD, available from Hilton-Davis, located in Italy; the 2-(4-styryl-phenyl)-2H-naphthol[1,2-d]triazoles; 4,4'-bis-(1,2,3-triazol-2-yl)-stilbenes; 4,4'-bis(styryl)bisphenyls; and the y-aminocoumarins. Specific examples of these brighteners include 4-methyl-7-diethylamino coumarin; 1,2-bis(-benzimidazol-2-yl)ethylene; 1,3-diphenylphrazolines; 2,5-bis(benzoxazol-2-yl)thiophene; 2-styryl-naphth[1,2-d]oxazole; and 2-(stilbene-4-yl)-2H-naphtho-[1,2-d]triazole.

Other optical brighteners which may be useful in the present invention include those disclosed in U.S. Pat. No. 3,646,015, issued Feb. 29, 1972 to Hamilton, the disclosure of which is incorporated herein by reference.

Suds Suppressors

Compounds known, or which become known, for reducing or suppressing the formation of suds can be incorporated into the compositions of the present invention. The incorporation of such materials, hereinafter "suds suppressors," can be desirable because the N-(1,2-propanediol) fatty acid amide surfactants hereof can increase suds stability of the detergent compositions. Suds suppression can be of particular importance when the detergent compositions include a relatively high sudsing surfactant in combination with the N-(1,2-propanediol) fatty acid amide surfactant. Suds suppression is particularly desirable for compositions intended for use in front loading automatic washing machines. These machines are typically characterized by having drums, for containing the laundry and wash water, which have a horizontal axis and rotary action about the axis. This type of agitation can result in high suds formation and, consequently, in reduced cleaning performance. The use of suds suppressors can also be of particular importance under hot water washing conditions and under high surfactant concentration conditions.

A wide variety of materials may be used as suds suppressors in the compositions hereof. Suds suppressors are well known to those skilled in the art. They are generally described, for example, in Kirk Othmer Encyclopedia of Chemical Technology, Third Edition, Volume 7, pages 430-447 (John Wiley & Sons, Inc., 1979). One category of suds suppressor of particular interest encompasses monocarboxylic fatty acids and soluble salts thereof. These materials are discussed in U.S. Pat. No. 2,954,347, issued Sep. 27, 1960 to Wayne St. John, said patent being incorporated herein by reference. The monocarboxylic fatty acids, and salts thereof, for use as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts. These material s are a preferred category of suds suppressor for detergent compositions.

The detergent compositions may also contain non-surfactant suds suppressors. These include, for example, list: high molecular weight hydrocarbons such as paraffin, fatty acid esters (e.g., fatty acid triglycerides), fatty acid esters of monovalent alcohols, aliphatic $C_{18}$-$C_{40}$ ketones (e.g. stearone), etc. Other suds inhibitors include N-alkylated amino triazines such as tri- to hexaalkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g. K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 5° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo, et al., incorporated herein by reference. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed of fused onto the silica. Silicone suds suppressors are well known in the art and are, for example, disclosed in U.S. Pat. No. 4,265,779, issued May 5, 1981 to Gandolfo et al and European Patent Application No. 89307851.9, published Feb. 7, 1990, by Starch, M. S., both incorporated herein by reference.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al., issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1500 cs. at 25° C.;
(ii) from about 5 to about 50 parts per 100 parts by weight of (i) of siloxane resin composed of $(CH_3)_3 SiO_{\frac{1}{2}}$ units of $SiO_2$ units in a ratio of from $(CH_3)_3 SiO_{\frac{1}{2}}$ units and to $SiO_2$ units of from about 0.6:1 to about 1.2:1; and
(iii) from about ]to about 20 parts per 100 parts by weight of (i) of a solid silica gel;

For any detergent compositions to be used in automatic laundry washing machines, suds should not form to the extent that they overflow the washing machine. Suds suppressors, when utilized, are preferably present in a "suds suppressing amount." By "suds suppressing amount" is meant that the formulator of the composition can select an amount of this suds controlling agent that will sufficiently control the suds to result in a low-sudsing laundry detergent for use in automatic laundry washing machines. The amount of suds control will vary with the detergent surfactants selected. For example, with high sudsing surfactants, relatively more of the suds controlling agent is used to achieve the desired suds control than with lesser foaming surfactants. In general, a sufficient amount of suds suppressor should be incorporated in low sudsing detergent compositions so that the suds that form during the wash cycle of the automatic washing machine (i.e., upon agitation of the detergent in aqueous solution under the intended wash temperature and concentration conditions) do not exceed about 75% of the void volume of washing machine's containment drum, preferably the suds do not exceed about 50% of said void volume, wherein the void volume is determined as the difference between total volume of the containment drum and the volume of the water plus the laundry.

The compositions hereof will generally comprise from 0% to about 5% of suds suppressor. When utilized as suds suppressors, monocarboxylic fatty acids, and salts thereof, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphates are generally utilized in amounts ranging from about 0.1% to about 2%, by weight, of the composition.

Hydrocarbon suds suppressors are typically utilized in amounts ranging from about 0.01% to about 5.0%, although higher levels can be used.

In addition to the foregoing ingredients which are generally employed in fabric laundry, dishwashing and hard surface cleaners for cleansing and sanitizing purposes, the glycerol amide surfactant compositions herein can also be used with a variety of other adjunct ingredients which provide still other benefits in various compositions within the scope of this invention. The following illustrates a variety of such adjunct ingredients, but is not intended to be limiting thereof.

Fabric Softeners

Various through-the-wash fabric softeners, especially the impalpable smectite clays of U.S. Pat. No. 4,062,647, Storm and Nirschl, issued Dec. 13, 1977, as well as other softener clays known in the art, can be used typically at levels of from about 0.5% to about 10% by weight in the present compositions to provide fabric softener benefits concurrently with fabric cleaning. The glucose amides of the present invention cause interference with the softening performance of the clay than do the common polyethylene oxide nonionic surfactants of the art. Clay softeners can be used in combination with amine and cationic softeners, as disclosed, for example, in U.S. Pat. No. 4,375,416, Crisp et al., Mar. 1, 1983 and U.S. Pat. No. 4,291,071, Harris et al, issued Sep. 22, 1981.

Hair Care Ingredients

Shampoo compositions formulated in the manner of this invention can contain from about 0.05% to about 10% by weight of various agents such as: conditioners, e.g., silicones (see, for example, U.S. Pat. Nos. 4,152,416 and 4,364,847); antidandruff agents such as the pyridinethiones, especially zinc pyridinethione (see U.S. Pat. Nos. 4,379,753 and 4,345,080), selenium compounds such as selenium sulfide and OCTOPIROX; hair styling polymers (see U.S. Pat. Nos. 4,012,501 and 4,272,511); and pediculicides (anti-lice agents) such as LINDANE and various pyrethrins (see British Patent 1,593,601 and U.S. Pat. No. 4,668,666).

Polyhydroxy Fatty Acid Amides

The N-(1,2-propanediol) fatty acid amides can be used in combination with polyhydroxy fatty acid amide compounds, which are nonionic surfactants conveniently available from renewable resources. Such surfactants have the general formula $R^2C(O)NR^3Z$, wherein $R^2$ is typically $C_7$-$C_{19}$ alkyl or alkenyl, preferably $C_9$-$C_{17}$ alkyl or alkenyl, $R^3$ is typically —$CH_3$, —$C_2H_5$ or —$C_3H_7$ or —$CH_2CH_2OH$ and Z is a polyhydroxyhydrocarbyl moiety having a linear hydrocarbyl chain with at least three hydroxyls affixed to said chain. Z is preferably derived from a reducing sugar such as glucose, fructose, maltose, xylose, lactose or mixtures thereof. See U.S. Pat. Nos. 2,703,798 and 2,965,576. Use of the glycerol amide surfactants herein admixed with said polyhydroxy fatty acid amides at weight ratios typically in the range of 5:1 to 1:5 provides high sudsing compositions especially useful as high sudsing dishwashing liquids. Such mixtures are typically used at levels of from about 5% to about 50% by weight of such liquid compositions, together with anionic surfactants and other ingredients noted herein.

Other Ingredients

A wide variety of other ingredients useful in detergent compositions can be included in the compositions hereof, including other active ingredients, carriers, hydrotropes, processing aids, dyes or pigments, solvents for liquid formulations, etc.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used.

The detergent compositions hereof will preferably be formulated such that during use in aqueous cleaning operations, the wash water will have a pH of between about 6.5 and about 11, preferably between about 7.5 and about 10.5. Liquid product formulations preferably have a pH between about 7.5 and about 9.5, more preferably between about 7.5 and about 9.0. Techniques for controlling pH at recommended usage levels include the use of buffers, alkalis, acids, etc., and are well known to those skilled in the art.

This invention further provides a method for cleaning substrates, such as fibers, fabrics, hard surfaces, skin, etc., by contacting said substrate, with a detergent composition comprising detersive enzyme and one or more artionic, nonionic, or cationic surfactants, wherein said detergent composition contains an enzyme performance-enhancing amount of N-(1,2-propanediol) fatty acid amide, typically at least about 1%, by weight, of the composition, in the presence of a solvent such as water or water-miscible solvent (e.g., primary and secondary alcohols). Agitation is preferably provided for enhancing cleaning. Suitable means for providing agitation include rubbing by hand or preferably with use of a brush, sponge, cloth, mop, or other cleaning device, automatic laundry washing machines, automatic dishwashers, etc.

The following examples further illustrate the practice of this invention, but are not intended to be limiting thereof.

EXAMPLE I

PREPARATION OF HEAPD AND REACTION WITH METHYL LAURATE

Step 1: Reaction of glycidol (50.0 g) with ethanol amine (45.32 g; Aldrich) to prepare 3-[2-(hydroxyethyl)amino]-1,2-propanediol ("HEAPD").

Glycidol is added under nitrogen to a cooled stirring solution of neat ethanolamine. The rate of addition is adjusted to keep the solution below 20° C.. After half of the glycidol is added the reaction mixture becomes so viscous that stirring stops. Ethanol (47.5 g, 50 wt %) is added and the addition of glycidol is continued; the reaction is allowed to warm slowly to room temperature. The ethanol and untreated ethanol amine are removed by vacuum distillation. The product does not distill at 130° C. (internal temperature) under full vacuum, so the pale yellow hazy liquid is used directly in further reactions. Characterization by TLC (80 $CHCl_3$:23 MeOH:3 $NH_4OH$) showed two products. The desired HEAPD amine can be purified by Kugelrohr distillation at 165°-175° C., and characterized by $C_{13}$ n.m.r. and GC.

Step 2: The HEAPD prepared in the foregoing manner (13.5 g) is reacted with methyl laurate (P&G CE 1295; 21.4 g) to provide the corresponding amide, as follows.

The HEAPD amine, the ester, methanol (3.5 g, 10 wt %) and sodium methoxide (2.16 g, 10 mole %) are mixed in a small jar. A stirbar is added and the jar is sealed. The reaction is heated to (70°-75° C.) in an oil bath with stirring. About 5 minutes after the mixture is completely heated the two phases mix and slowly become clear. The mixture is cooled, poured into an evaporating dish, and dried in a vacuum oven. TLC after 5 hours of drying shows unreacted ester in about the same ratio as amide, but no free amine. The desired amide product is precipitated from acetone and is redried.

The following Examples II(a)–II(c) illustrate the preparation of 3-methylamino-1,2-propanediol (MAPD) which can be subsequently reacted with fatty acid esters to provide detersive surfactants for use in this invention.

EXAMPLE II (a) Preparation of MAPD from 100 g 3-chloro-1,2-propanediol (Aldrich) and 351.2 g monomethylamine (MMA; 40% in water; Aldrich).

The chlorodiol is added to the amine at room temperature and the reaction is run without cooling. After 20 minutes the temperature is at 64° C. After 5 hours the reaction cools back to room temperature, and the excess MMA and water are removed at 60° C. on a rotovap. The product is dissolved in methanol and sodium methoxide (50%) is added to bring the pH to 11.3. After sitting for 5 hours, NaCl precipitate is filtered off. The product solution is evaporated (rotovap) to give a solid as a semi-liquid. Characterized by IR and C13 n.m.r.

(b) Preparation of MAPD from 185.2 g glycidol (Aldrich) and 1176.7 g MMA (33% in ethanol; Fluka).

Glycidol is added to a cooled (ice water bath, solution at 1 C.) stirring solution of MMA. The glycidol is added over I hour to ensure that the temperature does not exceed 20° C. The reaction is kept in an ice bath for 2½ hours and then allowed to warm to room temperature overnight. The ethanol is removed on the rotovap and the product is purified by kugelrohr distillation at 120° C. to give a clear viscous liquid. Characterized by GC (99%) and C13 n.m.r.

(c) Preparation of MAPD from 50.0 g glycidol and 78.28 g MMA (40% in water; Aldrich).

Glycidol is added to a cooled (ice water bath, solution at 7° C.) stirring solution of MMA. The glycidol is added over 2 hours with care so that the reaction remains below 20° C.. The solution is kept in the ice bath for 1 hour and then the water is removed at 85° C. for 1 hour on the rotovap. 50 mL of methanol are added and then are removed on the rotovap. The product is purified by kugelrohr distillation at 115°–125° C. to give a clear viscous liquid; characterization is by G.C. and n.m.r.

EXAMPLE III

PREPARATION OF HARDENED TALLOW AMIDE OF MAPD

Reactants: 10.51 g. 3-Methylamino-1,2-propanediol (MAPD) 28.83 g Hardened Tallow Methyl Ester The ester is melted with stirring in a sealed jar. After 3–4 minutes' cooling, the MAPD, methanol (2.16 g, 0.068 mole, 10 wt.%) and sodium methoxide (2.16 g, 25% in MeOH, 10 mole %) are added. The resealed jar is heated to 78° C. in an oil bath. After 20 minutes, the hazy mixture clears and the jar is removed from the oil bath. The reaction mixture solidifies overnight and the product is dried in a vacuum oven and ground to give a waxy solid. Characterization is done by IR and TLC, GC and C13 n.m.r.

EXAMPLE IV

PREPARATION OF HARDENED TALLOW AMIDE OF HEAPD

Reactants: 20.25 g. 3-hydroxyethylamino-1,2-propanediol (HEAPD) 38.88 g Hardened Tallow Methyl Ester The HEAPD, ester, methanol (6.2 g, 0.19 mole, 10 wt. %) and sodium methoxide (2.92 g of 25% solution in methanol, 10 mol %) are mixed in a jar. A stirbar is added and the jar is sealed. The reaction is heated to reflux (75° C.) with stirring in an oil bath. The reaction clears once at temperature (20 minutes) except for solid HEAPD. An additional 5 minutes of heating is used to dissolve all of the amine, and then the jar is removed from the oil bath. The pale yellow solution begins to solidify after 30 minutes and is completely solid after sitting overnight. The product is dried in a vacuum oven and ground to give a waxy solid. Characterization is by GC and n.m.r. spectroscopy.

EXAMPLE V

PREPARATION OF PALMITATE AHIDE OF MAPD

Reactants: 7.5 g MAPD 19.3 g Methyl Palmitate (Aldrich; 97%)

The MAPD, methyl palmitate and methanol (2.68 g, 1.2 equiv.) are heated to 43° C. under argon. Once the ester melts, stirring is started and the solution is heated to 80° C. Sodium methoxide catalyst (0.57 g of 25% in methanol, 0.04 equiv.) is added and the reaction is heated for 1 hour. The methanol is distilled to give the product as a waxy solid.

EXAMPLE VI

PREPARATION OF LAURAMIDE OF MAPD

Reactants: 21.55 g of MAPD 43.88 g methyl laurate CE 1295

Methanol (6.5 g, 0.68 equiv.) and MAPD are mixed until homogeneous and the ester is added. The reaction is heated with stirring under argon to reflux (78° C.) and sodium methoxide catalyst (2.5 g 25% in methanol, 0.05 equiv.) is added. Almost immediately the hazy solution turns clear and there is a slight drop in internal temperature. After heating for 1 hour at 80° C., the methanol is removed by distillation and the compound is pumped at 90° C. under vacuum for 20 minutes. The product is poured into an evaporating dish and dried in a vacuum oven at room temperature for 2 hours. The compound solidifies upon stirring and is dried further by pump vacuum overnight, ground and dried for 1 hour in a vacuum oven at 22° C. (room temperature).

Products from the foregoing reactions which are substantially free (less than about 2%) of unreacted fatty acids are preferred for use in detergent compositions where high sudsing is desired.

The following Examples illustrate various compositions encompassed by this invention, but are not intended to be limiting thereof.

EXAMPLE VII

A laundry detergent containing enzymes but without LAS surfactant is as follows.

| Ingredients | Wt. % |
|---|---|
| C14–15 alkyl polyethoxylate (2.25) sulfonic acid | 21.00 |
| Palmitate Amide of MAPD[1] | 7.00 |
| Sodium tartrate mono- and di-succinate (80:20 mix) | 4.00 |
| Citric acid | 3.80 |
| C12–14 fatty acid | 3.00 |
| Tetraethylene pentaamine ethoxylate(15–18) | 1.50 |
| Ethoxylated copolymer of polyethylene - polypropylene terephthalate polysulfonic acid | 0.20 |
| Protease B (34 g/l)[2] | 0.68 |
| Lipase (1OOKLU/g)[3] | 0.47 |
| Cellulase (5000 cevu/g)[4] | 0.14 |
| Brightener 36[5] | 0.15 |
| Ethanol | 5.20 |
| Monoethanolamine | 2.00 |
| Sodium formate | 0.32 |
| 1,2 propane diol | 8.00 |
| Sodium hydroxide | 3.10 |
| Silicone suds suppressor | 0.0375 |
| Boric acid | 2.00 |
| Water/misc. | Balance to 100 |

[1]Prepared as disclosed above.
[2]Protease B is a modified bacterial serine protease described in European Patent Application Serial No. 87 303761 filed April 28, 1987, particularly pages 17, 24 and 98.
[3]Lipase used herein is the lipase obtained by cloning the gene from *Humicola lanuginosa* and expressing the gene in *Aspergillus oryzae*, as described in European Patent Application 0 258 068, commercially available under the trade name LIPOLASE (ex Novo Nordisk A/S, Copenhagen Denmark).
[4]Cellulase used herein is sold under the trademark CAREZYME (Novo Nordisk, A/S, Copenhagen Denmark).
[5]Brightener 36 is commercially available as TINOPAL TAS 36. The brightener is added to the composition as a separately prepared pre-mix of brightener (4%), monoethanolamine (60%) and water (35.5%).

EXAMPLE VIII

A liquid laundry detergent composition suitable for use at the relatively high concentrations common to front-loading automatic washing machines, especially in Europe, and over a wide range of temperatures is as follows.

| Ingredient | Weight % |
|---|---|
| Lauramide of MAPD | 14 |
| C$_{14-15}$EO(2.25) sulfate, Na salt | 10.0 |
| C$_{14-15}$EO(7) | 4.0 |
| C$_{12-14}$ alkenylsuccinic anhydride[1] | 4.0 |
| C$_{12-14}$ fatty acid* | 3.0 |
| Citric acid (anhydrous) | 4.6 |
| Protease (enzyme)[2] | 0.37 |
| Termamyl (enzyme)[3] | 0.12 |
| Lipolase (enzyme)[4] | 0.36 |
| Carezyme (enzyme)[5] | 0.12 |
| Dequest 2060S[6] | 1.0 |
| NaOH (pH to 7.6) | 5.5 |
| 1,2 propanediol | 4.7 |
| Ethanol | 4.0 |
| Sodium metaborate | 4.0 |
| CaCl$_2$ | 0.014 |
| Ethoxylated tetraethylene pentamine[7] | 0.4 |
| Brightener[8] | 0.13 |
| Silane[9] | 0.04 |
| Soil release polymer[10] | 0.2 |
| Silicone (suds control)[11] | 0.4 |
| Silicone dispersant[12] | 0.2 |
| Water and minors | Balance |

[1]As SYNPRAX 3 from ICI or DTSA from Monsanto.
[2]As Protease B as described in EPO 0342177 November 15, 1989, percentage at 40 g/l.
[3]Amylase, from NOVO; percentage at 300 KNU/g.
[4]Lipase, from NOVO; percentage at 100 KLU/g.
[5]Cellulase from NOVO; percentage at 5000 CEVU/l.
[6]Available from Monsanto.
[7]From BASF as LUTENSOL P6105.
[8]BLANKOPHOR CPG766, Bayer.
[9]Silane corrosion inhibitor, available as A1130 from Union Carbide or DYNASYLAN TRIAMINO from Hüls.
[10]Polyester, per U.S. Pat. No. 4,711,730.
[11]Silicone suds control agent available as Q2-3302 from Dow Corning.
[12]Dispersant for silicone suds control agent available as DC-3225C from Dow Corning.
*Preferred fatty acid is topped palm kernel, comprising 12% oleic acid and 2% each of stearic and linoleic.

A modern condensed laundry granule is as follows.

| Ingredient | Weight % |
|---|---|
| C$_{14-15}$ alkyl alcohol sulfonic acid | 13 |
| C$_{14-15}$ alkyl polyethoxy (2.25) sulfonic acid | 5.60 |
| C$_{12-13}$ alkyl polyethoxylate (6.5) | 1.45 |
| Tallow Amide of MAPD | 2.50 |
| Sodium aluminosilicate (as hydrated Zeolite A) | 25.2 |
| Crystalline layered silicate builder[1] | 23.3 |
| Citric acid | 10.0 |
| Sodium carbonate | To get wash pH=9.90 |
| Sodium polyacrylate (m.w. 2000-4500) | 3.2 |
| Diethylenetriamine pentaacetic acid | 0.45 |
| Savinase[2] | 0.70 |
| 6-Nonanoylamino-6-oxo-peroxycaproic acid | 7.40 |
| Sodium perborate monohydrate | 2.10 |
| Nonanoyloxybenzene sulfonic acid | 5.00 |
| Brightener | 0.10 |

[1]Layered silicate builders are known in the art. Preferred are the layered sodium silicates. See, for example, the layered sodium silicate builders of U.S. Pat. No. 4,664,859, issued May 12, 1987 to H. P. Rieck, incorporated herein by reference. A suitable layered silicate builder is available as SKS-6 from Hoechst.
[2]Available from Novo Nordisk A/S, Copenhagen.

The composition of Example X can be modified by replacing the sulfonated polyethoxylate with C$_{12-14}$ alkyl benzene sulfonate.

The following Example illustrates a heavy duty liquid detergent composition.

| Ingredients | Weight % |
|---|---|
| C$_{14-15}$ alkyl polyethoxylate (2.25) sulfonic acid | 19.50 |
| C$_{12-14}$ alkyl ester sulfonic acid, methyl ester | 2.00 |
| Lauramide of MAPD | 6.50 |
| Sodium tartrate mono- and di-succinate (80:20 mix) | 4.00 |
| Citric acid | 3.80 |
| C$_{12-14}$ fatty acid | 3.00 |
| Tetraethylene pentaamine ethoxylate (15-18) | 1.50 |
| Ethoxylated copolymer of polyethylene - polypropylene terephthalate polysulfonic acid | 0.20 |
| Protease B (34 g/l)[2] | 0.68 |
| Lipase (100KLU/g)[3] | 0.47 |
| Cellulase (5000 cevu/g)[4] | 0.14 |
| Brightener 36[5] | 0.15 |
| Ethanol | 5.20 |
| Monoethanolamine | 2.00 |
| Sodium formate | 0.32 |
| 1,2 propane diol | 8.00 |
| Sodium hydroxide | 3.10 |
| Silicone suds suppressor | 0.0375 |
| Boric acid | 2.00 |
| Water/misc. | Balance to 100 |

[1]Prepared as disclosed above.
[2]Protease B is a modified bacterial serine protease described in European Patent Application Serial No. 87 303761 filed April 28, 1987, particularly pages 17, 24 and 98.
[3]Lipase used herein is the lipase obtained by cloning the gene from *Humicola lanuginosa* and expressing the gene in *Aspergillus oryzae*, as described in European Patent Application 0 258 068, commercially available under the trade name LIPOLASE (ex Novo Nordisk A/S, Copenhagen Denmark).
[4]Cellulase used herein is sold under the trademark CAREZYME (Novo Nordisk, A/S, Copenhagen Denmark).
[5]Brightener 36 is commercially available as TINOPAL TAS 36. The brightener can be premixed with the monoethanolamine and water (4.5% brightener, 60% MEA, 35.5% H$_2$O) and added to the composition.

The following Examples illustrate Mg$^{++}$ or Ca$^{++}$ liquid-containing compositions which are especially suitable for "light-duty" use, such as for dishwashing.

EXAMPLE XI A-D

| Ingredients | Percent (wt.) | | | |
|---|---|---|---|---|
| | A | B | C | D |
| C$_{12-14}$ alkyl ethoxy sulfate (1 EO) | 16 | 9 | 12 | — |
| C$_{12-14}$ alkyl ethoxy sulfate (3 EO) | — | 14 | — | 11 |
| C$_{10}$ alkyl ethoxylate (8EO) | 7 | 3 | 7 | 1 |
| Lauramide of MAPD | 8 | 9 | 12 | 6 |
| Coconut diethanolamide | — | — | — | 5 |
| Dimethyl dodecyl amine oxide | — | 1 | — | 2 |
| Cocoamidopropyl hydroxysultaine | — | 1 | 3 | — |
| Cocoamidopropyl betaine | 2 | — | — | — |
| Mg$^{2+}$* | — | — | 1 | 1 |
| Ca$^{2+}$* | 0.5 | 1 | — | — |
| Sodium toluene sulfonate | 3 | 3 | 3 | 3 |
| Ethanol | 4 | 4 | 4 | 4 |
| Water | Balance | | | |

*Added as MgCl$_2$ or CaCl$_2$, respectively.

For compositions where especially high sudsing is desired (e.g., dishwashing), it is preferred that less than about 5%, preferably less than about 2%, most preferably no C$_{14}$ or higher fatty acids be present, since these can suppress sudsing. Accordingly, the formulator of high sudsing compositions will desirably avoid the introduction of suds-suppressing amounts of such fatty acids into high sudsing compositions with the glycerol fatty acid amide, and/or avoid the formation of C$_{14}$ and higher fatty acids on storage of the finished compositions. One simple means is to use C$_{12}$ ester reactants to prepare the fatty acid glycerol amides herein. Fortunately, the use of amine oxide or sulfobetaine surfactants can overcome some of the negative sudsing effects caused by the fatty acids. In another mode, the "crude" fatty acid glycerol amide surfactant containing free fatty acids can be subjected to a further reaction with, for example, monoethanolamine, in the presence of 6%–10% methanol solvent at 65° C.–85° C. to convert the acids to their corresponding ethanolamides, which do not inhibit sudsing.

EXAMPLE XII

A conditioning shampoo is as follows. The method of manufacture noted is generally acceptable for preparing the other shampoo compositions herein. However, shampoo formulators will appreciate that variations in manufacturing methods are possible.

| Component | Weight % |
|---|---|
| Coconutalkyl (EO)$_3$ sulfate (NH$_4$ salt) | 13.5 |
| Palmitate Amide of MAPD[1] | 3.5 |
| Ethylene glycol distearate | 3.0 |
| Dimethicone[2] | 1.0 |
| Ammonium chloride | 3.00 |
| Tricetyl methyl ammonium chloride | 0.50 |
| Cetyl alcohol | 0.42 |
| Stearyl alcohol | 0.18 |
| Citric acid | 0.16 |
| Perfume | 0.65 |
| Preservative (GLYDANT) | 5 ppm |
| Water (double reverse osmosis) | Balance |

[1]Prepared per above.
[2]1:1 (wt.) mixture silicone gum:silicone fluid.

In a typical manufacturing procedure a premix containing the silicone hair conditioning agent is prepared. The premix comprises alkylethoxylated sulfate heated to 170° F. (77° C.) ±10° to which is added a portion of the stearyl alcohol at the same temperature, to which is then added a portion of the cetyl alcohol at the same temperature, with mixing for a minimum of about 20 minutes. The temperature is then increased to 180° F. (82° C.) before silicone addition. The silicone is then added at 180° F. (82° C.) ±5° and mixed for 60 minutes.

A mix is prepared using water at 170° F. (77° C.) ±10° to which is added the fatty acid glycerol amide surfactant at the same temperature, to which is subsequently added a portion of the cetyl alcohol and a portion of the stearyl alcohol, respectively, at the same temperature, followed by addition of the ethylene glycol distearate at that temperature, followed by the addition of the tricetyl methyl ammonium chloride, at which time the system is mixed for a minimum of about 11 minutes ±3 minutes, typically over a range from about 8 minutes to about 35 minutes. The silicone premix is added at 170° F. (77° C.) ±10°. The preservative is then added at the same temperature and mixing is continued for 5–30 minutes.

The balance of the ingredients are then added, generally at about 80° F. (27.5° C.) to provide the final product.

EXAMPLE XIII

An antidandruff shampoo is as follows.

| Ingredients | Weight % |
|---|---|
| Coconutalkyl amide of HEAPD | 20.0 |
| Ammonium C$_{12-18}$ alkyl sulfate | 5.0 |
| Ammonium C$_{14-18}$ alkyl (EO)$_3$ sulfate | 9.0 |
| Ethylene glycol distearate | 5.0 |
| Zinc pyridinethione[1] | 1.0 |
| Sodium citrate | 0.5 |
| Monoethanolamine | 3.0 |
| Citric acid | 0.2 |
| Color/perfume | 0.4 |

| Ingredients | Weight % |
|---|---|
| Water | Balance |

[1]Per U.S. Pat. No. 4,345,080.

Soap bar compositions comprising from about 1% to about 10% by weight of the glycerol amides herein, from about 75% to about 85% by weight of a C$_{12}$–C$_{18}$ fatty acid soap in the sodium potassium, ammonium or alkanol ammonium salt form, and up to about 12% by weight of water show excellent hardness and reduced "smear" qualities. The following examples illustrate such a toilet bar for skin cleansing purposes.

EXAMPLE XIV

| Ingredients | Weight % |
|---|---|
| Palmitate Amide of MAPD | 3.00 |
| Fatty Acid Soap* | 83.75 |
| NaCl | 0.44 |
| Minors (perfume, etc.) | 2.5 |
| Water | Balance |

*Sodium salts of mixed tallow/stearic/coconut fatty acids at a weight ratio of 70/10/20.

EXAMPLE XV

A soap bar of somewhat softer, but higher sudsing, quality is prepared by replacing the MAPD amide of Example XIV with an equivalent amount of the tallow amide of HEAPD.

EXAMPLE XVI

A high sudsing liquid composition which is especially useful as a hand dishwashing detergent is as follows.

| Ingredients | Weight |
|---|---|
| C$_{10}$ alkyl ethoxylate (8 EO) | 7.0 |
| C$_{12-14}$ alkyl ethoxy sulfate (1 EO) | 12.0 |
| Coconutalkyl N-methylglucamide | 6.0 |
| Coconutalkyl HEAPD | 4.0 |
| C$_{10-14}$ alkyl polyglucoside (avg. glucose 2.5) | 3.0 |
| Mg Cl$_2$ | 1.0 |
| Sodium toluene sulfonate | 3.0 |
| Ethanol | 4.0 |
| Water | Balance |

The above composition can be modified by adding about 0.2% of a suds control agent to provide a hard surface cleaner for walls and other environmental surfaces.

What is claimed is:

1. A cleaning composition, comprising:
   (a) from about 1% to about 30% by weight of an N-1,2-propanediol) fatty acid amide surfactant of the formula

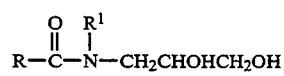

wherein R is a C$_7$–C$_{21}$ hydrocarbyl species and R$^1$ is a C$_1$–C$_6$ hydrocarbyl or substituted hydrocarbyl species;
   (b) at least about 1% by weight of one or more non-amide detersive surfactants;

(c) from 0% to about 50% by weight of a detergency builder;
(d) from 0% to about 5% by weight of a detersive enzyme;
(e) from 0% to about 25% by weight of active adjunct materials; and
(f) the balance of the composition comprising moisture and carrier ingredients.

2. A composition according to claim 1 wherein R is selected from coconut, palm, tallow fatty alkyl and oleyl hydrocarbyl species and wherein $R^1$ is selected from methyl and hydroxyethyl species.

3. A composition according to claim 1 wherein the non-amide detersive surfactant is a member selected from the group consisting of alkyl benzene sulfonate surfactants, alkyl sulfate surfactants, alkyl ether sulfate surfactants, amine oxide surfactants, ethoxylated alcohol surfactants, ethoxylated alkyl phenol surfactants, alkyl polyglucoside surfactants, fatty acid soap, and mixtures thereof.

4. A composition according to claim 1 which contains at least about 3% by weight of a non-phosphate detergency builder.

5. A composition according to claim 1 which contains at least about 0.1% of a detersive enzyme.

6. A composition according to claim 1 which contains at least about 5% by weight of a bleaching ingredient selected from bleaches and mixtures of bleaches with bleach activators as the active adjunct material.

7. A composition according to claim 1 which contains a soil release polymer as the active adjunct material.

8. A composition according to claim 1 which contains a member selected from the group consisting of sources of magnesium ions, sources of calcium ions, and mixtures thereof, as the active adjunct material.

9. A composition according to claim 1 which additionally contains a fabric softening ingredient.

10. A composition according to claim 1 which additionally contains a bleach.

11. A composition according to claim 10 wherein the bleach is a perborate, percarbonate, persulfate, or phthalocyanine bleach, or mixtures thereof.

12. A liquid detergent composition, comprising:
(a) at least about 3% by weight of one or more anionic detersive surfactants;
(b) at least about 0.3% by weight of a source of magnesium ions, calcium ions, or mixtures thereof;
(c) at least about 3% by weight of an N-(1,2-propanediol) fatty acid amide surfactant of the formula

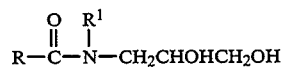

wherein R is a $C_7$–$C_{21}$ hydrocarbyl species and $R^1$ is selected from methyl, hydroxyethyl and mixtures thereof; and
(d) a liquid carrier.

13. A liquid detergent according to claim 12 which additionally contains a surfactant which is a fatty acid amide of a polyhydroxyamine having 3 or more hydroxy groups on a single carbon chain attached to said amine.

* * * * *